(12) United States Patent
Kühn

(10) Patent No.: US 8,496,795 B2
(45) Date of Patent: Jul. 30, 2013

(54) ELECTROCHEMICAL GAS SENSOR WITH AT LEAST ONE PUNCTIFORM MEASURING ELECTRODE

(75) Inventor: Uwe Kühn, Wesenberg (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 1344 days.

(21) Appl. No.: 11/843,259

(22) Filed: Aug. 22, 2007

(65) Prior Publication Data
US 2008/0116083 A1    May 22, 2008

(30) Foreign Application Priority Data
Nov. 22, 2006   (DE) .......................... 10 2006 054 947

(51) Int. Cl.
*G01N 27/413*   (2006.01)

(52) U.S. Cl.
USPC ............................ 204/415; 204/416; 204/409

(58) Field of Classification Search
USPC ................. 73/31.05; 204/409, 412, 414–416, 204/431–432; 205/780.5, 782–783, 785.5, 205/786, 794.5
See application file for complete search history.

(56) References Cited

U.S. PATENT DOCUMENTS

| 4,171,253 | A | * | 10/1979 | Nolan et al. ................. 204/411 |
| 4,406,770 | A | * | 9/1983 | Chan et al. .................... 204/406 |
| 5,126,035 | A | * | 6/1992 | Kiesele et al. ................ 204/415 |
| 5,281,324 | A | * | 1/1994 | Kiesele et al. ................ 204/415 |
| 5,650,054 | A | * | 7/1997 | Shen et al. .................... 204/412 |
| 2002/0033334 | A1 | * | 3/2002 | Tschuncky et al. .......... 204/415 |
| 2002/0121438 | A1 | * | 9/2002 | Saffell et al. .................. 204/415 |
| 2003/0150725 | A1 | * | 8/2003 | Tschuncky .................... 204/415 |
| 2004/0134780 | A1 | * | 7/2004 | Inoue et al. ................... 204/424 |
| 2005/0034987 | A1 | * | 2/2005 | Zhou et al. .................... 204/426 |

FOREIGN PATENT DOCUMENTS

| DE | 19845318 A1 | 4/2000 |
| DE | 198 45 318 C2 | 9/2000 |
| DE | 101 44 862 B4 | 3/2003 |
| EP | 0 266 432 A1 | 5/1988 |
| EP | 0 266 432 B1 | 5/1988 |
| EP | 0 783 687 B1 | 5/1999 |
| GB | 2318874 A | 5/1998 |
| GB | 2342168 A | 4/2000 |
| GB | 2380261 A | 4/2003 |
| GB | 2421578 A | 6/2006 |
| WO | WO 2007/020410 A1 | 2/2007 |

OTHER PUBLICATIONS

"Electrochemical Series", http://www.hbcpnetbase.com/, May 13, 2012.*

* cited by examiner

*Primary Examiner* — Keith Hendricks
*Assistant Examiner* — Bach Dinh
(74) *Attorney, Agent, or Firm* — McGlew and Tuttle, P.C.

(57) ABSTRACT

An electrochemical gas sensor with a plurality of electrodes is provided with an electrolyte, with a gas-permeable membrane (1), with a gas-permeable and conductive carrier layer (2) applied to the membrane (1) and with at least one measuring electrode (3) applied to the carrier layer (2). The measuring electrode (3) is of a punctiform design and the electrochemical potential difference of the reaction between the carrier layer (2) and the measuring electrode (3) is at least 20 mV, can be manufactured in a compact form and makes possible an especially low power consumption for measured gases in the percentage range.

8 Claims, 2 Drawing Sheets

ELECTROCHEMICAL GAS SENSOR WITH AT LEAST ONE PUNCTIFORM MEASURING ELECTRODE

CROSS REFERENCE TO RELATED APPLICATIONS

This application claims the benefit of priority under 35 U.S.C. §119 of German Patent Application DE 10 2006 054 947.3 filed Nov. 22, 2006, the entire contents of which are incorporated herein by reference.

FIELD OF THE INVENTION

The present invention pertains to an electrochemical gas sensor with at least one punctiform measuring electrode.

BACKGROUND OF THE INVENTION

In an electrochemical gas sensor for a gas to be measured, for example, oxygen in the air, each arriving oxygen molecule is reacted electrochemically at a measuring electrode. To limit the signal current, the supply of oxygen is reduced by permeation through closed membranes or by diffusion through capillaries, or the electrochemical reaction takes place at so-called microelectrodes. The manufacture of microelectrodes is expensive because the participation of the electrical contacts or contacting in the electrochemical reaction must be ruled out or the electrochemically active measuring electrode surface must not change in terms of its size in order to ensure that reproducible measured values are obtained.

The manufacture of such microelectrodes is carried out, for example, by embedding a wire in a synthetic resin or fusion in glass or even by etching or growth techniques.

Examples of such microelectrodes can be found in EP 0 266 432 B1. However, even oxygen sensors equipped with membranes or capillaries still yield undesiredly high signal currents of about 200 µA during the admission of air, which leads to the need to increase the battery capacity in portable gas-measuring devices in order to obtain the long service life desired.

Furthermore, closed membranes and long capillaries lead to an undesired prolongation of the response time.

SUMMARY OF THE INVENTION

The object of the present invention is to provide a compact electrochemical gas sensor of a simple design with a markedly reduced signal current and without additional capillaries or closed membranes with the associated drawbacks such as prolonged response time being used.

According to the invention, an electrochemical gas sensor is provided comprising a housing having an opening. A plurality of electrodes are provided as well as an electrolyte that is provided in the housing. A gas-permeable membrane is provided as well as a gas-permeable and conductive carrier layer applied to the membrane and with at least one measuring electrode applied to the carrier layer, wherein the measuring electrode has a punctiform design and the electrochemical potential difference of the reaction between the carrier layer and the measuring electrode differs by at least 20 mV.

The essential advantage of the gas sensor according to the invention arises from the fact that only signal currents in the percentage range occur, so that the power consumption of the gas sensor is substantially reduced.

The gas-permeable membrane used preferably consists of a hydrophobic polymer such as PTFE, PP or PE, to which a gas-permeable and electrically conductive carrier layer consisting of a metal, a conductive polymer or a carbon material such as diamond-like carbon (DLC), was applied.

By applying a suitable reduction potential to the punctiform measuring electrode on the carrier layer, this can be used especially as an oxygen-active measuring electrode.

If the measuring electrode consists of iridium particles or contains iridium and the electrochemically necessary oxidation potential for ammonia is set, the gas sensor acts as an ammonia sensor and makes it possible to measure gas concentration measurements at high measured gas concentrations in air with relatively low signal currents of less than 20 µA. A measuring electrode size of one square mm or less can be obtained by selecting the size of the material particles applied.

Two exemplary embodiments of the present invention will be explained below on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiment of the invention is illustrated.

DESCRIPTION OF THE PREFERRED EMBODIMENT

Figure 1:
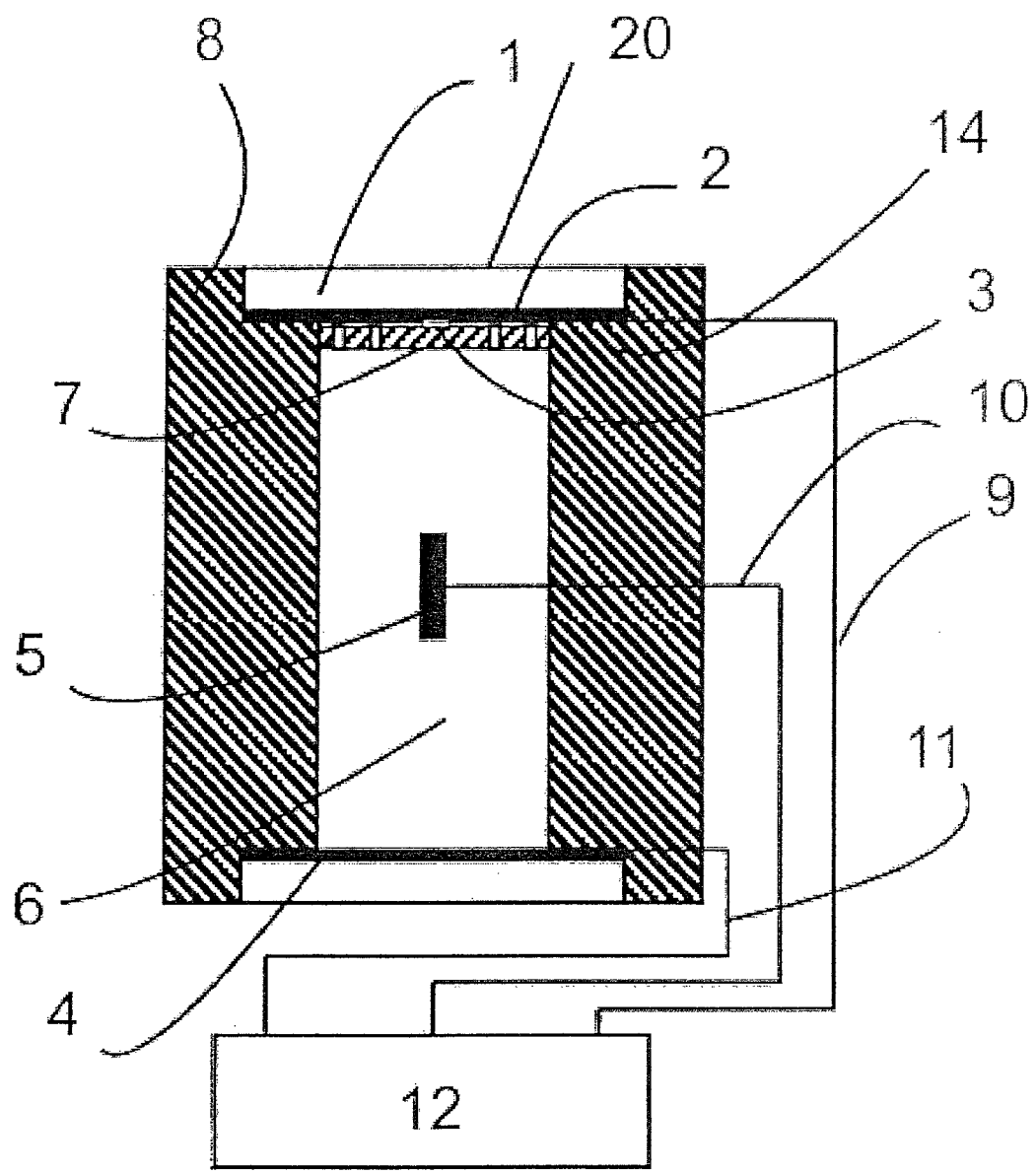
FIG. 1 is a vertical section through a cylindrical electrochemical gas sensor.

Referring to the drawings in particular, the electrochemical gas sensor in FIG. 1 has a housing 8 consisting of a plastic, which encloses the electrolyte space 6 containing an electrolyte. The counterelectrode 4, the reference electrode 5 and the measuring electrode array 20 composed of the partial components 1, 2, 3 are located in the electrolyte space.

The electrodes are connected to a potentiostat and evaluating unit 12 via drain wires 9, 10, 11 consisting of metal.

The measuring electrode array 20 has a gas-permeable membrane 1 consisting of polytetrafluoroethylene (PTFE), polypropylene (PP) or polyethylene (PE) with a gas-permeable and an electrically conductive carrier layer 2, which is applied thereto, and is electrochemically inactive based on the potential set and consists especially of a carbon material such as diamond-like carbon (DLC).

The carrier layer 2 may consist of metal, but it must be inactive in the electrochemical potential range characteristic of the gas to be measured. The carrier layer 2 is also used as a contact aid over the sealing area 14 to the drain wire 9. The drain wire 9 of the measuring electrode array 20 must not come into connection with the electrolyte in the electrolyte space 6 and must be protected from this by sealing measures such as bonding or welding. The electrochemically active measuring electrode 3 proper of a punctiform design is applied to the conductive carrier layer 2. The size of the punctiform extension of the measuring electrode 3 depends on the specific measurement task and can be selected correspondingly. It is also possible to use a plurality of punctiform measuring electrodes 3 in a gas sensor, in which case the two-dimensional extension of each punctiform measuring electrode is on the order of magnitude of about one square mm.

The measuring electrode 3 preferably consists of a precious metal such as silver, gold, platinum and has an area of less than one square mm for a gas sensor for measuring oxygen in air.

For an ammonia sensor, the measuring electrode 3 consists of iridium and its area may be greater than one square mm.

The electrolyte space 6 is filled with an electrolyte solution called briefly "electrolyte," such as sulfuric acid, phosphoric acid or salt solutions (halides of the alkali or alkaline earth metals) or even organic electrolytes.

A diffusion barrier 7 consisting of a perforated plastic part or a hydrophilic mat is preferably placed behind the measuring electrode array 20 in order to minimize the back diffusion of the gas being measured from the electrolyte space 6.

The carrier layer 2 may be designed in the form of a wire, a fiber or a tube and the punctiform measuring electrode 3 may be applied to the membrane-side end of the carrier layer 2.

Figure 2:
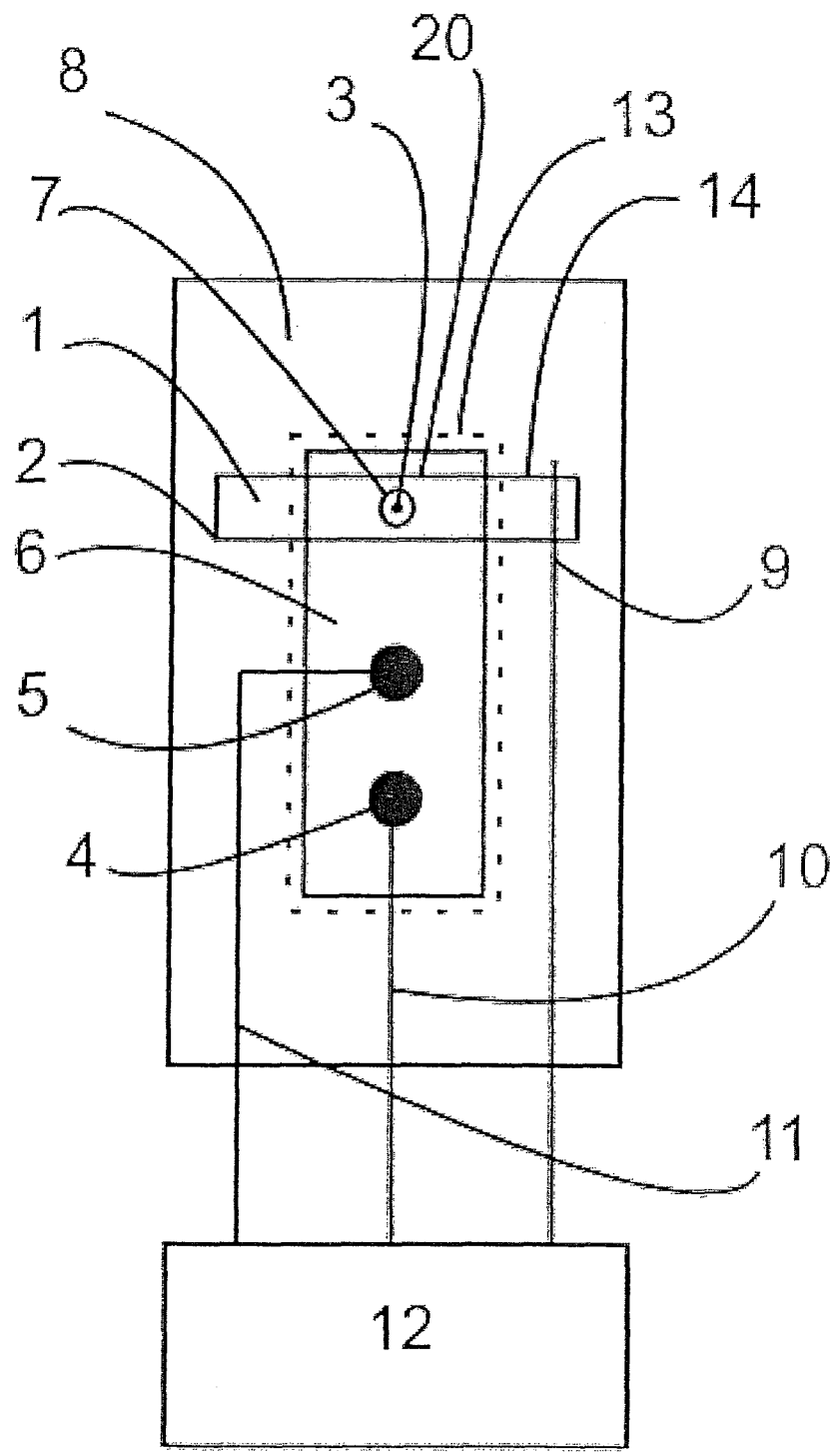
FIG. 2 is a top view of a gas sensor of a planar design.

FIG. 2 shows an electrochemical gas sensor of a planar design with a housing 8, which is laminated from two plastic films. This construction also has a counterelectrode 4, a reference electrode 5 and a measuring electrode array 20, which comprises an inactive carrier layer 2 applied to a gas-permeable plastic 1 on the underside and a punctiform measuring electrode 3, likewise on the underside of the array.

The analyte, i.e., the gas to be measured, is transported to the measuring electrode 3 via a hole 77 in the film. The measuring electrode 3 may also be of a rectangular shape and is connected to the drain wire 9 via the sealing area 14. All electrodes are connected to the potentiostat and evaluating unit 12 via the drain wires 9, 10, 11.

An electrolyte carrier 66, which is impregnated with electrolyte and consists of a porous and hydrophilic mat, is located in the electrolyte area 13.

It is not necessary to use a diffusion barrier in this design because the diffusion paths are sufficiently long.

The electrolytes used correspond to those described above. The dimensioning of the measuring electrode 3 corresponds to the description given so far for FIG. 1. It is important for all embodiments that the electrochemical potential difference for the electrochemical detection reaction between the carrier layer 2 and the measuring electrode 3 is at least 20 mV.

While specific embodiments of the invention have been shown and described in detail to illustrate the application of the principles of the invention, it will be understood that the invention may be embodied otherwise without departing from such principles.

What is claimed is:

1. An electrochemical gas sensor comprising:
    a housing defining an electrolyte space having an opening;
    an electrolyte located in said electrolyte space of said housing, said electrolyte comprising a flowable electrolyte solution;
    a gas-permeable membrane formed of a hydrophobic material and closing said opening, said gas-permeable membrane having an electrolyte facing side;
    a gas-permeable and conductive carrier layer with a side facing said gas-permeable membrane, said conductive carrier layer being applied as a layer on said electrolyte facing side of said gas-permeable membrane, said conductive carrier layer having an electrolyte facing side, opposite to said side facing said gas-permeable membrane, forming a carrier contact surface, said carrier contact surface being exposed to environmental gas outside of said housing via said opening, via said gas-permeable membrane and via said gas-permeable and conductive carrier layer;
    a drain wire extending trough said housing, said drain wire being electrically connected to said conductive carrier layer so as to not come into connection with said electrolyte in the electrolyte space;
    a plurality of electrodes in contact with said electrolyte, said electrodes including a measuring electrode applied to said carrier contact surface of said conductive carrier layer, said measuring electrode having an electrode contact surface that is in electrical contact with said carrier contact surface of said conductive carrier layer and said measuring electrode being electrically connected to said drain wire via said conductive carrier layer, said electrode contact surface of said measuring electrode being small compared to said carrier contact surface of said conductive carrier layer surrounding said electrode contact surface, said electrode contact surface being on the order of magnitude of about one square millimeter and an electrochemical potential difference of a reaction between said carrier layer and said measuring electrode differing by at least 20 mV, wherein said carrier layer consists essentially of one or more of a metal, a conductive polymer, a carbon material and diamond like carbon.

2. An electrochemical gas sensor in accordance with claim 1, wherein said measuring electrode comprises one or more of silver, gold or platinum, a silver alloy, a gold alloy and a platinum alloy.

3. An electrochemical gas sensor in accordance with claim 1, wherein said measuring electrode comprises one or more of iridium and an iridium alloy.

4. An electrochemical gas sensor in accordance with claim 1, further comprising:
    additional drain wires, wherein one of said electrodes is a reference electrode and another of said electrodes is a counterelectrode, one of said additional drain wires being connected to said reference electrode and another of said additional drain wires being connected to said counterelectrode; and
    a potentiostat and evaluating unit connected to each of said drain wires.

5. An electrochemical gas sensor comprising:
    a housing defining an electrolyte space having an opening;
    an electrolyte located in said electrolyte space of said housing, said electrolyte comprising a flowable electrolyte solution;
    a gas-permeable membrane formed of a hydrophobic material and closing said opening, said gas-permeable membrane having an electrolyte facing side;
    a gas-permeable and conductive carrier layer with a side facing said gas-permeable membrane, said conductive carrier layer being applied as a layer on said electrolyte facing side of said gas-permeable membrane, said conductive carrier layer having an electrolyte facing side, opposite to said side facing said gas-permeable membrane, forming a carrier contact surface, said carrier contact surface being exposed to environmental gas outside of said housing via said opening, via said gas-permeable membrane and via said gas-permeable and conductive carrier layer;
    a drain wire extending trough said housing, said drain wire being electrically connected to said conductive carrier layer so as to not come into connection with said electrolyte in the electrolyte space;

a plurality of electrodes in contact with said electrolyte, said electrodes including a measuring electrode applied to said carrier contact surface of said conductive carrier layer, said measuring electrode having an electrode contact surface that is in electrical contact with said carrier contact surface of said conductive carrier layer and said measuring electrode being electrically connected to said drain wire via said conductive carrier layer, said electrode contact surface of said measuring electrode having a surface area less than 1 square mm. and an electrochemical potential difference of a reaction between said carrier layer and said measuring electrode differing by at least 20 mV, wherein said carrier layer consists essentially of one or more of a metal, a conductive polymer, a carbon material and diamond like carbon.

6. An electrochemical gas sensor in accordance with claim 5, wherein said measuring electrode comprises one or more of silver, gold or platinum, a silver alloy, a gold alloy and a platinum alloy.

7. An electrochemical gas sensor in accordance with claim 5, wherein said measuring electrode comprises one or more of iridium and an iridium alloy.

8. An electrochemical gas sensor in accordance with claim 5, further comprising:

additional drain wires, wherein one of said electrodes is a reference electrode and another of said electrodes is a counterelectrode, one of said additional drain wires being connected to said reference electrode and another of said additional drain wires being connected to said counterelectrode; and a potentiostat and evaluating unit connected to each of said drain wires.

* * * * *